(12) United States Patent
Huss et al.

(10) Patent No.: US 7,001,918 B2
(45) Date of Patent: Feb. 21, 2006

(54) 7-PYRROLYL TETRACYCLINE COMPOUNDS AND METHODS OF USE THEREOF

(75) Inventors: Sophie Huss, Madrid (ES); Jose M. Bueno, Madrid (ES); Jose M. Fiandor, Madrid (ES); Roger Frechette, Reading, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 10/858,616

(22) Filed: Jun. 1, 2004

(65) Prior Publication Data

US 2004/0248857 A1 Dec. 9, 2004

Related U.S. Application Data

(63) Continuation of application No. 10/636,436, filed on Aug. 6, 2003, now abandoned, which is a continuation of application No. 10/295,417, filed on Nov. 15, 2002, now abandoned, which is a continuation of application No. 10/097,135, filed on Mar. 12, 2002, now abandoned.

(30) Foreign Application Priority Data

Mar. 13, 2001 (EP) .................................. 01500064

(51) Int. Cl.
| | | |
|---|---|---|
| A61K 31/402 | (2006.01) | |
| C07C 237/26 | (2006.01) | |
| C07D 207/335 | (2006.01) | |
| C07D 207/30 | (2006.01) | |
| C07D 295/033 | (2006.01) | |

(52) U.S. Cl. ...................... 514/427; 514/381; 514/399; 514/406; 548/255; 548/529; 552/203; 552/204; 552/205

(58) Field of Classification Search ................. 548/529, 548/255; 552/203, 204, 205; 514/427, 381, 514/399, 406
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,062,717 A | 11/1962 | Hammer | |
| 3,148,212 A | 9/1964 | Boothe et al. | |
| 3,165,531 A | 1/1965 | Blackwood et al. | |
| 3,226,436 A | 12/1965 | Petisi et al. | |
| RE26,253 E | 8/1967 | Petisi et al. | |
| 3,338,963 A | 8/1967 | Petisi et al. | |
| 3,341,585 A | 9/1967 | Bitha et al. | |
| 3,345,379 A | 10/1967 | Martell | |
| 3,345,410 A | 10/1967 | Winterbottom | |
| 3,403,179 A | 9/1968 | Zambrano | |
| 3,454,697 A | 7/1969 | Joyner et al. | |
| 3,518,306 A | 6/1970 | Martell | |
| 3,557,260 A | 1/1971 | Weber et al. | |
| 3,579,579 A | 5/1971 | Hvalka et al. | |
| 3,862,225 A | 1/1975 | Lloyd et al. | |
| 3,901,942 A * | 8/1975 | Bernardi et al. | ............ 552/205 |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 5,021,407 A | 6/1991 | Levy | |
| 5,281,628 A | 1/1994 | Hlavka et al. | |
| 5,284,963 A | 2/1994 | Sum et al. | |
| 5,328,902 A | 7/1994 | Sum et al. | |
| 5,380,888 A | 1/1995 | Sum et al. | |
| 5,386,041 A | 1/1995 | Sum et al. | |
| 5,401,729 A | 3/1995 | Sum et al. | |
| 5,401,863 A | 3/1995 | Hlavka et al. | |
| 5,420,272 A | 5/1995 | Sum et al. | |
| 5,430,162 A | 7/1995 | Sum et al. | |
| 5,457,096 A | 10/1995 | Sum et al. | |

(Continued)

FOREIGN PATENT DOCUMENTS

EP    0 536 346    4/1993

(Continued)

OTHER PUBLICATIONS

Koza, D. and Nsiah, Y., "Palladium catalyzed C-N Bond Formation in the Synthesis of 7-Amino-Substituted Tetracyclines," J. Org. Chem., vol. 67, pp. 5025-5027 (2002), at p. 5026, 2nd col., compound 2f.*

(Continued)

*Primary Examiner*—Golam M. M. Shameem
*Assistant Examiner*—Anthony J. Paviglianiti
(74) *Attorney, Agent, or Firm*—Lahive & Cockfied, LLP; Elizabeth A. Hanley, Esq.; Cynthia M. Soroos, Esq.

(57) ABSTRACT

A compound of Formula (I): wherein variables R, $R^1$, $R^2$, $R^3$ and A are as defined in the

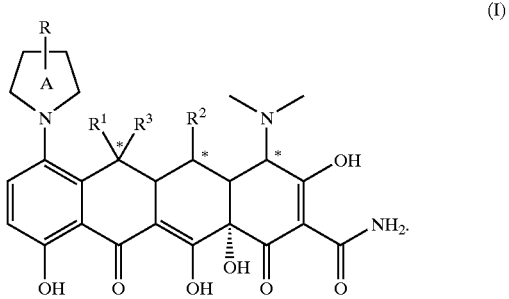

(I)

17 Claims, No Drawings

U.S. PATENT DOCUMENTS

| | | | |
|---|---|---|---|
| 5,466,684 A | | 11/1995 | Sum et al. |
| 5,494,903 A | | 2/1996 | Hlavka et al. |
| 5,495,018 A | * | 2/1996 | Sum et al. ............... 544/63 |
| 5,495,031 A | | 2/1996 | Sum et al. |
| 5,512,553 A | | 4/1996 | Sum et al. |
| 5,530,117 A | | 6/1996 | Hlavka et al. |
| 5,532,227 A | | 7/1996 | Golub et al. |
| 5,789,395 A | | 8/1998 | Amin et al. |
| 5,834,450 A | | 11/1998 | Su |
| 5,886,175 A | | 3/1999 | Sum et al. |
| 6,500,812 B1 | * | 12/2002 | Nelson et al. ............ 514/152 |
| 6,642,270 B1 | * | 11/2003 | Nelson et al. ............ 514/464 |
| 6,683,068 B1 | | 1/2004 | Nelson et al. |
| 6,818,634 B1 | | 11/2004 | Nelson et al. |
| 6,818,635 B1 | | 11/2004 | Nelson et al. |
| 2002/0128237 A1 | * | 9/2002 | Nelson et al. ............ 514/152 |
| 2004/0214800 A1 | * | 10/2004 | Levy et al. ............... 514/152 |
| 2004/0242548 A1 | * | 12/2004 | Draper et al. ............. 514/152 |
| 2005/0038002 A1 | * | 2/2005 | Nelson et al. ............ 514/152 |

FOREIGN PATENT DOCUMENTS

| | | | |
|---|---|---|---|
| EP | | 0 536 515 | 4/1993 |
| EP | | 0 582 788 | 2/1994 |
| EP | | 0 582 789 | 2/1994 |
| EP | | 0 582 790 | 2/1994 |
| EP | | 0 582 810 | 2/1994 |
| GB | | 1469384 | 4/1977 |
| WO | | WO 00/28983 A1 | 5/2000 |
| WO | | WO 200204404 A2 * | 1/2002 |
| WO | | WO 200204407 A2 * | 1/2002 |
| WO | | WO 2004038000 A2 * | 5/2004 |
| WO | | WO 2004038001 A2 * | 5/2004 |
| WO | | WO 2004064728 A2 * | 8/2004 |
| WO | | WO 2004091513 A2 * | 10/2004 |

OTHER PUBLICATIONS

Koza, D. and Nsiah, Y., "Palladium Catalyzed C-N Bond Formation in the Synthesis of 7-Amino-Substituted Tetracyclines," J. Org. Chem., vol. 67(14), pp. 5025-5027 (Jul. 2002), at p. 5026, Figure 1, compounds 2f, 2g, 2h, 2i.*

Koza, D.J. "Synthesis of 7-substituted tetracycline derivatives," Org. Lett. 2(6):815-17 (2000).

* cited by examiner

7-PYRROLYL TETRACYCLINE COMPOUNDS AND METHODS OF USE THEREOF

RELATED APPLICATIONS

This application is a continuation of U.S. Ser. No. 10/636,436, filed Aug. 6, 2003 now abandoned; which is a continuation of U.S. patent application Ser. No. 10/295,417, filed Nov. 15, 2002 now abandoned; which is a continuation U.S. patent application Ser. No. 10/097,135, filed Mar. 12, 2002 now abandoned; which claims priority to European Patent Application Serial No. 01500064.9, filed on Mar. 13, 2001. The entire contents of each of the aforementioned applications are hereby incorporated herein by reference in their entirety.

FIELD OF THE INVENTION

The present invention relates to a novel class of chemical compounds and to their use in medicine. In particular, the invention concerns novel tetracycline derivatives, methods for their preparation, pharmaceutical compositions containing them and their use as antibiotic agents.

BACKGROUND OF THE INVENTION

Tetracycline derivatives are known for treating bacterial infections. However, there remains a need for tetracycline derivatives for the treatment of Gram-positive, Gram-negative and community acquired infections. Moreover, there remains a need for tetracycline derivatives effective against tetracycline resistant strains.

DETAILED DESCRIPTION OF THE INVENTION

The present invention provides compounds of Formula (I):

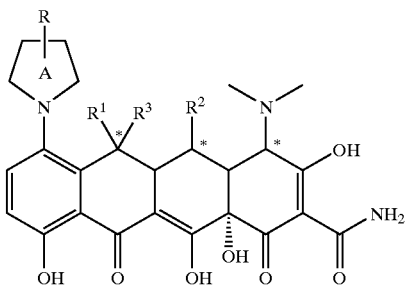

wherein:
A represents an aromatic 5 membered heterocycle, optionally containing, in addition to the nitrogen atom indicated in Formula (I), one to three additional nitrogen atoms and optionally substituted by one or more groups "R" selected from
halogen,
—NRaRb,
$C_{1-6}$ alkyl,
$C_{2-6}$ alkenyl,
$C_{3-6}$ alkynyl,
aryl,
heteroaryl,
hydroxy,
—$OC_{1-6}$ alkyl,
formyl,
cyano,
trifluoromethyl,
—CHNORa,
—$CO_2$Ra,
—CONRaRb,
—NRaC(O)Ra,
—NRaC(O)ORa,
—OC(O)NRaRb,
—OC(O)Ra,
—OC(O)ORa,
or a $C_{1-6}$alkyl group substituted by one or more groups selected from
hydroxy,
—NRaRb,
—$OC_{1-6}$alkyl,
—SRa,
—CHNOR,
—$CO_2$Ra,
—CONRaRb,
—NRaC(O)Ra,
—NRaC(O)ORa,
—OC(O)NRaRb,
—OC(O)Ra,
—OC(O)ORa Ra and Rb independently represent hydrogen or $C_{1-6}$-alkyl (preferably methyl);

$R^1$ represents hydrogen, $C_{1-6}$-alkyl or together $R^1$ and $R^3$ represent a $CH_2$ moiety;

$R^2$ represents hydrogen, —$OC_{1-6}$alkyl, —$O(O)C_{1-6}$alkyl or hydroxy;

$R^3$ represents hydrogen, hydroxy or together $R^3$ and $R^1$ represent a $CH_2$ moiety;

and pharmaceutically acceptable derivatives and solvates thereof.

Compounds of Formula (I) contain at least one asymmetric centre, denoted by *, and thus may exist as enantiomers or diastereoisomers. It is to be understood that the invention includes each such isomer, either in substantially pure form or admixed in any proportion with one or more other isomers of the compounds of Formula (I). The preferred stereochemistry at the centre where $R^1$ and $R^3$ are substituents is when $R^1$ is H, $R^3$ is in the alpha-configuration (downwards). The preferred stereochemistry at the centre where $R^2$ is a substituent is alpha (downwards). The preferred stereochemistry at the centre where $N(Me)_2$ is a substituent in the ring is alpha (downwards).

The term "pharmaceutically acceptable derivative" as used herein refers to any pharmaceutically acceptable salt, or metabolically labile derivative of a compound of Formula (I), for example a derivative of an amine group, which, upon administration to the recipient, is capable of providing (directly or indirectly) a compound of Formula (I). It will be appreciated by those skilled in the art that the compounds of Formula (I) may be modified to provide pharmaceutically acceptable derivatives thereof at any of the functional groups in the compounds of Formula (I). Such derivatives are clear to those skilled in the art, without undue experimentation, and with reference to the teaching of Burger's Medicinal Chemistry And Drug Discovery, 5th Edition, Vol 1: Principles And Practice, which is incorporated herein by reference. For example compounds of Formula (I) may be N-alkylated in the presence of formaldehyde and an amine such as methylamine to give the corresponding Mannich base adducts.

Salts and solvates of compounds of Formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of Formula (I) and their pharmaceutically acceptable derivatives, and solvates.

Suitable salts according to the invention include those formed with both organic and inorganic acids or bases. Pharmaceutically acceptable acid addition salts include those formed from trifluoroacetic, hydrochloric, hydrobromic, hydroiodoic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic, and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Suitable solvates according to the invention include hydrates.

The term alkyl, as used herein to define a group or a part of a group, unless otherwise stated, refers to a saturated straight or branched alkyl chain containing from 1 to 6 carbon atoms. Examples of such groups include without limitation methyl, ethyl, n-propyl, isopropyl, n-butyl, isobutyl, sec-butyl, tert-butyl, neopentyl and hexyl.

The term "alkenyl", as used herein to define a group or a part of a group, unless otherwise stated, refers to a straight or branched alkenyl chain containing from 2 to 6 carbon. Examples of such groups include without limitation 1-ethenyl, 1-propenyl, allyl(2-propenyl), 1-butenyl, 2-butenyl, 2-pentenyl.

The term "alkynyl", as used herein to define a group or a part of a group, unless otherwise stated, refers to a straight or branched alkynyl chain containing from 3 to 6 carbon. Examples of such groups include without limitation propynyl, butynyl or pentynyl.

The term "cycloalkyl" as used herein to define a group or a part of a group, unless otherwise stated, refers to a saturated alkyl ring containing from 3 to 6 carbon atoms. Examples of such groups include cyclopropyl, cyclobutyl, cyclopentyl and cyclohexyl.

The term "halogen" refers to a fluorine, chlorine, bromine or iodine atom. Suitably the halogen atom is selected from chlorine, bromine or iodine, preferably chlorine or bromine. Chlorine is most preferred.

The term "aryl group" refers to an aromatic mono or bicyclic ring system comprising from 5 to 10 carbon atoms and heteroaryl group is wherein one or more of the carbon atoms is/are replaced by heteroatoms independently selected from nitrogen, oxygen and sulfur, Suitably A represents pyrrole, pyrazole, 1,2,3-triazole, 1,2,4-triazole and tetrazole.

Preferred substituents on A include ethoxycarbonyl, carboxaldehyde, cyano, dimethylaminomethyl, oxime and methyloxime.

Suitably, $R^2$ is selected from hydrogen, methoxy and hydroxy. More suitably, $R^2$ is selected from hydrogen and hydroxy. Conveniently, $R^2$ is hydroxy. Preferably, $R^2$ is hydrogen.

Suitably, $R^3$ represents hydrogen or methyl. Conveniently $R^3$ is methyl. Preferably $R^3$ is hydrogen.

Suitably the compound of Formula (I) is derivatised from a natural tetracycline like compound. Examples of natural tetracycline like compounds include tetracycline, chlortetracycline, oxytetracycline, demeclocycline, methacycline, sancycline, doxycycline, and minocycline. Preferably the natural tetracycline like compound is selected from sancycline and doxycycline, most preferably sancycline.

It is to be understood that the present invention covers all combinations of suitable, convenient and preferred groups described hereinabove.

References herein after to compounds of the invention include compounds of Formula (I) and their pharmaceutically acceptable derivatives and solvates.

Examples of compounds of Formula (I) include:

[4(R,S)-(4aα,5aα,12aα)]-4-(Dimethylamino)-7-(1H-Tetrazol-1-yl)-1,4,4a,5,5a,6,11,12a-octahydro-3,10,12,12a-tetrahydroxy-1,11-dioxo-2-naphthacenecarboxamide

[4-S-(4aα,5aα,12aα)]-4-(Dimethylamino)-7-[(4-ethoxycarbonyl)-1H-triazol-1-yl]-1,4,4a,5,5a,6,11,12a-octahydro-3,10,12,12a-tetrahydroxy-1,11-dioxo-2-naphthacenecarboxamide

[4-S-(4aα,5aα,12aα)]-4-(Dimethylamino)-7-[(5-ethoxycarbonyl)-1H-triazol-1-yl,4,4a,5,5a,6, 11,12a-octahydro-3, 10,12,12a-tetrahydroxy-1,11-dioxo-2-naphthacenecarboxamide

[4S-(4aα,5aα, 12aα)]-4-(Dimethylamino)-7-(1H-pyrrol-1-yl-3-carboxaldehyde)-1,4,4a,5,5a,6,11,12a-octahydro-3, 10,12,12a-tetrahydroxy-1,11-dioxo-2-naphthacenecarboxamide

[4S-(4aα,5aα,12aα)]-4-(Dimethylamino)-7-(3-((hydroxymino)-methyl)-1H-pyrrol-1-yl)-1,4,4a,5,5a,6,11, 12a-octahydro-3, 10,12,12a-tetrahydroxy-1,11-dioxo-2-naphthacenecarboxamide

[4S-(4aα,5aα, 12aα)]-7-(3-Cyanopyrrol-1-yl)-4-(dimethylamino)-1,4,4a,5,5a,6,11,12a-octahydro-3, 10,12,12a-tetrahydroxy-1,11-dioxo-2-naphthacenecarboxamide

[4S-(4aα,5aα, 12aα)]-4-(Dimethylamino)-7-(3-((methyloxymino)methyl)-1H-pyrrol-1-yl)-1,4,4a,5,5a,6,11,12a-octahydro-3,10,12,12a-tetrahydroxy-1,11-dioxo-2-naphthacenecarboxamide As demonstrated in the assays described below the compounds of the present invention show activity against the most important pathogens, including gram positive bacteria such as *S. pneumoniae* and *S. aureus*, and gram negative organisms such as *H. influenzae, M catarrhalis* and *E. coli*. In addition, these compounds are active against gram positive and gram negative tetracycline resistant bacterial strains, including those with resistance mediated by efflux pumps and ribosome protection.

Accordingly, in a further aspect the present invention provides a method for the treatment of a tetracycline compound responsive state in a subject, preferably a human, which comprises administering to the subject an effective amount of a compound of Formula (I) or pharmaceutically acceptable derivative or solvate thereof.

In the alternative, there is provided a compound of Formula (I) or a pharmaceutically acceptable derivative or solvate thereof, for use in medical therapy, particularly, for use in the manufacture of a medicament for the treatment of a tetracycline compound responsive state.

The term "tetracycline compound responsive state" includes a state which can be treated, prevented, or otherwise ameliorated by the administration of a compound of Formula (I) or pharmaceutically acceptable derivative or solvate thereof. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important human and veterinary diseases such as respiratory tract infections, systemic infections and some local infections. More particulalry, compounds of the invention can be used to prevent or control diarrhoea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686–6690 (1988)). In one embodiment, the tetracycline compound is used to treat a bacterial infection. In a further embodiment, the tetracycline compound is used to treat a bacterial infection that is resistant to other tetracycline antibiotic compounds.

For the aviodance of doubt, the term 'treatment' as used herein includes prophylactic therapy.

Bacterial infections may be caused by a wide variety of gram positive and gram negative bacteria. The compounds of Formula (I) are useful as antibiotics against organisms which are resistant to other tetracycline compounds. The antibiotic activity of the compounds of Formula (I) may be determined using the method discussed in the Biological Example below, or by using the in vitro standard broth dilution method described in Waitz, J. A., *National Committee for Clinical Laboratory Standards*, Approved Standard M7-T2, vol. 10, no. 8, pp. 13–20, $2^{nd}$ edition, Villanova, Pa. (1990).

The compounds of the invention may also be used to treat infections traditionally treated with tetracycline compounds such as, for example, rickettsiae; a number of gram-positive and gram-negative bacteria; and the agents responsible for lymphogranuloma venereum, inclusion conjunctivitis and psittacosis. The compounds of Formula (I) may be used to treat infections of pneumococci, *Salmonella, E. coli, S. aureus* or *E. faecalis*.

The term "effective amount of the compound of Formula (I)" is that amount necessary or sufficient to treat or prevent a tetracycline compound responsive state. The effective amount can vary depending on such factors as the size and weight of the subject, the type of illness, or the particular tetracycline compound. One of ordinary skill in the art would be able to study the aforementioned factors and make the determination regarding the effective amount of the compound of Formula (I) or a pharmaceutically acceptable derivative or solvate thereof without undue experimentation.

The invention also pertains to methods of treatment against microorganism infections and associated diseases. The methods include administration of an effective amount of one or more compounds of Formula (I) or a pharmaceutically acceptable derivative or solvate thereof to a subject. Preferably the subject is a mammal e.g., a human.

For human use, a compound of the Formula (I) can be administered as raw drug substance, but will generally be administered in admixture with a pharmaceutically acceptable carrier selected with regard to the intended route of administration and standard pharmaceutical practice.

Accordingly, the present invention further provides a pharmaceutical formulation comprising a compound of Formula (I) or a pharmaceutically acceptable derivative or solvate thereof, and one or more pharmaceutically acceptable carriers.

The term pharmaceutically acceptable carrier includes substances capable of being coadministered with the compounds of Formula (I), and which allow performance of the intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc.

The pharmaceutical preparations can be sterilised and if desired mixed with auxiliary agents, e.g., lubricants, preservatives, stabilisers, wetting agents, emulsifiers, salts for influencing osmotic pressure, buffers, colourings, flavourings and/or aromatic substances and the like which do not deleteriously react with the compounds of the invention.

The compounds of the invention may be administered alone or in combination with pharmaceutically acceptable carriers or diluents. The compounds of the invention may be administered via oral, parenteral or topical routes. The administration may be carried out in single or multiple doses. The compounds of the invention may be administered in a wide variety of different dosage forms, for example they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions may be sweetened and/or flavoured. In general, the compounds of the invention are present in such dosage forms at concentration levels ranging from about 5.0% to about 70% by weight.

For oral administration, tablets may contain various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulphate and talc may be employed. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavouring agents, colouring matter or dyes, and, if so desired, emulsifying and/or suspending agents, together with diluents such as water, ethanol, propylene glycol, glycerin and various combinations thereof.

For parenteral administration (including intraperitoneal, subcutaneous, intravenous, intradermal or intramuscular injection), solutions of compounds of the invention in either sesame or peanut oil or in aqueous propylene glycol may be employed. The aqueous solutions may be buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral administration, examples of suitable preparations include solutions, preferably oily or aqueous solutions as well as suspensions, emulsions, or implants, including suppositories. Compounds of the invention may be formulated in sterile form in multiple or single dose formats. For example the compounds of the invention may be dispersed in a fluid carrier such as sterile saline or 5% saline dextrose solutions commonly used with injectables.

The compounds of the invention may be administered topically for example when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulphate 5% in water, and the like. In addition, materials such as anti-oxidants, humectants, viscosity stabilisers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats.

It will be appreciated that the actual amount of the compound of the invention used in a given therapy will vary according to the specific compound being utilised, the particular compositions formulated, the mode of application, the particular site of administration, etc. Optimal administration rates for a given protocol of administration can be readily ascertained by those skilled in the art without undue burden.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and, toxic effects. Thus, the conventionally recognised adverse reactions of gastrointestinal distress and inflammations, the renal toxicity, hypersensitivity reactions, changes in blood, and impairment of absorption through aluminium, calcium, and magnesium ions should be duly considered in the conventional manner.

The compounds and pharmaceutical compositions of the invention may be administered alone or in combination with other known compounds and compositions for treating tetracycline compound responsive states in a mammal e.g. a human. The term in combination with a known compound or composition is intended to include simultaneous, concomitant and sequential administration.

Accordingly, the present invention provides a combination comprising a compound of Formula (I) or a pharmaceutically acceptable derivative or solvate thereof, and a further active ingredient suitable for treating tetracycline compound responsive states in a mammal e.g. a human.

Compounds of Formula (I) and pharmaceutically acceptable derivatives and solvates thereof may be prepared by general methods outlined hereinafter where the groups R, $R^1$, $R^2$ and $R^3$ have the meaning defined for compounds of Formula (I) unless otherwise stated.

According to a further aspect of the invention, there is provided a process for preparing a compound of Formula (I) wherein A is a pyrrole ring optionally substituted by one or more group R or a pharmaceutically acceptable derivative or solvate thereof which process comprises reacting a compound of Formula (II) with a compound of Formula (III) wherein Ra and Rb are hydrogen or $C_{1-6}$alkyl under dehydrating conditions for example in the presence of sulphuric acid in methanol.

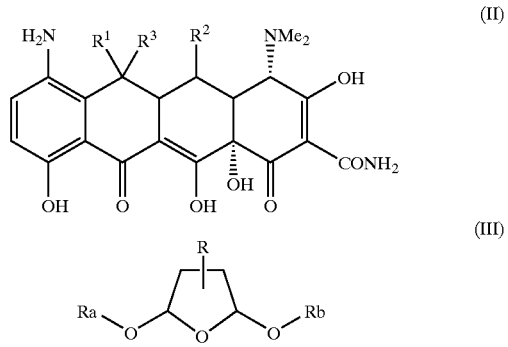

According to a further aspect of the invention, there is provided a process for preparing a compound of Formula (I) wherein A is a pyrrole ring optionally substituted by one or more group CHNORa or a pharmaceutically acceptable derivative or solvate thereof which process comprises reacting a compound of Formula (IV) with $NH_2ORa$ in water.

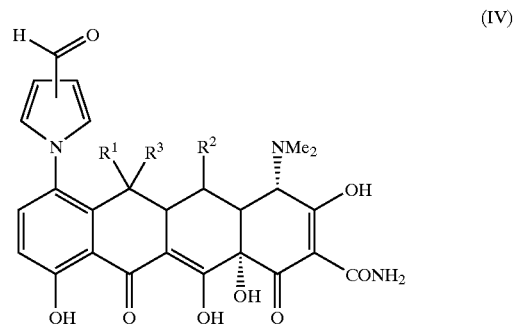

According to a further aspect of the invention, there is provided a process for preparing a compound of Formula (I) wherein A is a pyrrole ring optionally substituted by one or more group cyano or a pharmaceutically acceptable derivative or solvate thereof which process comprises reacting a compound of Formula (V) with acetic anhydride and formic acid.

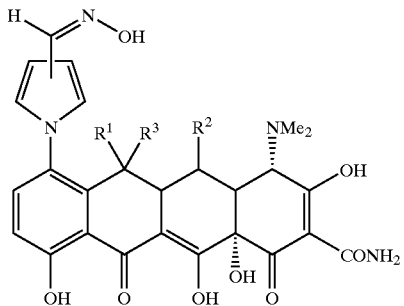

According to a further aspect of the invention, there is provided a process for preparing a compound of Formula (I) wherein A is a pyrrole ring optionally substituted by one or more group CH$_2$NRaRb or a pharmaceutically acceptable derivative or solvate thereof which process comprises reacting a compound of Formula (IV) with NHRaRb under dehydrating conditions for example in the presence of acetic acid, methanol and water and then subjecting the product to a reducing agent such as sodium cyanoborohydride.

According to a further aspect of the invention, there is provided a process for preparing a compound of Formula (I) wherein A is a tetrazole ring or a pharmaceutically acceptable derivative or solvate thereof which process comprises reacting a compound of Formula (II) with isobutyl nitrite in methanolic hydrochloric acid followed by treatment with a mixture containing sodium azide and triethyl orthoformate in acetic acid.

According to a further aspect of the invention, there is provided a process for preparing a compound of Formula (I) wherein A is a 1,2,3-triazole ring optionally substituted by one or more group CO$_2$Ra or a pharmaceutically acceptable derivative or solvate thereof which process comprises reacting a compound of Formula (II) with isobutyl nitrite in methanolic hydrochloric acid followed by treatment with sodium azide to afford the corresponding 7-azido intermediate, and then subjecting the 7-azido intermediate to a reaction with alkylpropiolate in dioxane under reflux conditions.

The invention will now be illustrated by way of the following Examples which should not be construed as constituting a limitation thereto.

EXAMPLE 1

[4(R,S)-(4aα,5aα,12aα)]-4-(Dimethylamino)-7-(1H-Tetrazol-1-yl)-1,4,4a,5,5a,6,11,12a-octahydro-3,10,12,12a-tetrahydroxy-1,11-dioxo-2-naphtacenecarboxamide A mixture of 7-amino-sancycline (50 mg), triethyl orthoformate (100 μl) and sodium azide (20 mg) in glacial acetic acid (5 ml) was heated to 80° C. for 2 h, then cooled to ambient temperature. This mixture was added dropwise at room temperature onto a solution of Isobutyl nitrite (60 μl) in 10 ml of methanolic hydrogen chloride (prepared by dissolving 0.83 ml of concentrated HCl in 100 ml of methanol). The solution was stirred at room temperature overnight, then poured onto diethyl ether and the resulting solid filtered-off and washed with diethyl ether. This material was purified by MPLC chromatography on silica gel C18. 10 mg of the pure material was isolated as a mixture 1:1 of two epimers at 4'-position.

MS (e.s.+): m/z 483 (M.$^+$+H)

$^1$H-NMR (CD$_3$OD): 9.42, 9.40(2s, 1H, H5'-Tetrazole); 7.60, 7.59 (2dd, 1H, H8, J$_1$=J$_2$=9 Hz); 7.06, 7.05 (2dd, 1H, H9, J$_1$=J$_2$=9 Hz); 4.81 (d, 0.5H, H4, J=3 Hz); 4.02(bs, 0.5H, H4)

EXAMPLE 2

[4-S-(4aα,5aα,12aα)]-4-(Dimethylamino)-7-[(4-ethoxycarbonyl)-1H-triazol-1-yl]-1,4,4a,5,5a,6,11,12a-octahydro-3,10,12,12a-tetrahydroxy-1,11-dioxo-2-naphthacenecarboxaminde

[4-S-(4aα,5aα, 12aα)]-4-(Dimethylamino)-7-[(5-ethoxycarbonyl)-1H-triazol-1-yl]-1,4,4a,5,5a,6,11,12a-octahydro-3,10,12,12a-tetrahydroxy-1,11-dioxo-2-naphthacenecarboxamide 1) Preparation of 7-azido-Sancycline:

To a suspension of 7-amino-Sancycline (50 mg) in 2 ml of methanolic hydrogen chloride (prepared by dissolving 0.83 ml of cc HCl into 100 ml of methanol) was added at 0° C. (ice-water bath) isobutyl nitrite (60 μl). The mixture was stirred at 0° C. for 1 h, then sodium azide (6.5 mg) was added at once. The mixture was stirred at r.t. for 2 h, then poured onto cold diethyl ether. The solid was filtered-off and washed with diethyl ether. 50 mg of 7-azido-Sancycline (m/z: 456, M.$^+$+H) was obtained as a powder, which was used withouth further purification.

2) Cycloaddition:

The above powder (50 mg) was suspended in dioxane (5 ml) and ethyl propiolate (100 μl) was added with stirring. The suspension was stirred for a few minutes at room temperature, then heated to reflux until HPLC analysis showed no remaining 7-azido-derivative (3 h aprox). The mixture was cooled down to room temperature and poured onto cold diethyl ether. The precipitate obtained was separated by filtration and washed with diethyl ether. The crude thus obtained was purified by preparative HPLC, affording a sample of 10 mg of a mixture of regioisomers.

MS (e.s.+): m/z 554 (M.$^+$+H)

[4S-(4aα,5aαα12aα)]-7-(Amino)-4-(dimethylamino)-1,4,4a,5,5a,6,11,12a-octahydro-3,10,12,12a-tetrahydroxy-1,11-dioxo-2-naphthacenecarboxamide (7 amino sancycline) is synthesised as described in U.S. Pat. No. 3,403,179

EXAMPLE 3

[4S-(4aα,5aαα, 12aα)]-4-(Dimethylamino)-7-(1H-pyrrol-1-yl-3-carboxaldehyde)-1,4,4a,5,5a,6,11,12a-octahydro-3,10,12,12a-tetrahydroxy-1,11-dioxo-2-naphthacenecarboxamide A mixture of 2,5-dimethoxy-3-tetrahydrofurancarboxaldehyde (0.35 ml) and 2.5M sulfuric acid (1.2 ml) was added dropwise to an open vessel containing a methanolic solution (10 ml) of the aniline (0.6 g) and stirred at room temperature for 2 h. The reaction mixture was precipitated in cold ether and filtrate to give a brown residue which was dissolved in water, freeze and lyophilised. The residue was purified using C18-F40 Biotage column chromatography. Pure compound (0.425 g) was obtained after lyophilisation of the appropriate fractions.

H-RMN (CD$_3$OD): 9.71(s, 1H, CHO), 7.61(bt, 1H, H-2pyrrole), 7.48(d, 1H, H-8, J=8.7 Hz), 6.95(d, 1H, H-9), 6.91(m, 1H, H-5pyrrole), 6.71(dd, 1H, H-4pyrrole, J=1.6 and 3.0 Hz), 4.01(d, 1H, H-4, J=1.1 Hz).

MS (e.s.+): m/z 508.15 (M$^+$+H)

EXAMPLE 4

[4S-(4aα,5aαα, 12aα)]4-(Dimethylamino)-7-(3-((hydroxymino)-methyl)-1H-pyrrol-1-yl)-1,4,4a,5,5a,6,11,12a-octahydro-3, 10,12,12a-tetrahydroxy-1,11-dioxo-2-naphthacenecarboxamide A water solution (12 ml) of carboxaldehyde (Example 3) (0.17 g) was stirred for 2 h in the presence of a two fold excess of hydroxylamine hydrochloride. The reaction mixture was freeze and lyophilised, and then filtrate on RP2 silica gel to give a 1:3 mixture of syn: anti isomers of the oxime in quantitative yield.

H-RMN (CD$_3$OD): syn isomer: 8.0(s, 1H, CH=N), 7.45 (d, 1H, H-8, J=8.7 Hz), 7.02(bt, 1H, H-2pyrrole), 6.93(d, 1H, H-9), 6.76(m, 1H, H-5pyrrole), 6.52(dd, 1H, H-4pyrrole, J=2.8 and 1.7 Hz), 4.02(bs, 1H, H-4).

H-RMN (CD$_3$OD): anti isomer: 7.52(bt, 1H, H-2pyrrole), 7.47(d, 1H, H-8, J=8.7 Hz), 7.27(s, 1H, CH=N), 6.93(d, 1H, H-9), 6.77(m, 1H, H-5pyrrole), 6.61(dd, 1H, H-4pyrrole, J=1.7 and 2.8 Hz), 4.02(bd, 1H, H-4, J=1.5 Hz).

MS (e.s.+): m/z 523.2 (M$^+$+H)

EXAMPLE 5

[4S-(4aα,5aαα12aα)]-7-(3-Cyanopyrrol-1-yl)-4-(dimethylamino)-1,4,4a,5,5a,6,11,12a-octahydro-3,10,12,12a-tetrahydroxy-1,11-dioxo-2-naphthacenecarboxamide The oxime (Example 4) (0.06 g) in a 1:1 mixture of acetic anhydride and formic acid (4 ml) was stirred at 90° C. for 2 h. The reaction mixture at room temperature was precipitated in cold ether and filtrate to give a brown residue which was dissolved in water, freeze and lyophilised. The residue was purified using a C8 Luna semi-preparative HPLC to give pure nitrile (0.027 g) as a yellow powder after lyophilisation of the appropriate fractions.

H-RMN (CD$_3$OD): 7.49(bt, 1H, H-2pyrrole), 7.47(d, 1H, H-8, J=8.7 Hz), 6.95(d, 1H, H-9), 6.90(dd, 1H, H-5pyrrole, J=2.1 and 2.8 Hz), 6.58(dd, 1H, H-4pyrrole, J=1.6 and 2.8 Hz), 4.01(bs, 1H, H-4).

MS (e.s.+): m/z 505.3 (M$^+$+H)

EXAMPLE 6

[4S-(4aα,5aα12aα)]-4-(Dimethylamino)-7-(3-((methyloxymino)methyl)-1H-pyrrol-1-yl)-1,4,4a,5,5a,6,11,12a-octahydro-3,10,12,12a-tetrahydroxy-1,11-dioxo-2-naphthacenecarboxamide A water solution (10 ml) of carboxaldehyde (Example 3) (0.085 g) was stirred for 2 h in the presence of a two fold excess of methoxylamine hydrochloride. The reaction mixture was freeze and lyophilised, and then purified using a C8 Luna semi-preparative HPLC. A 1:2 mixture of the syn:anti isomers of the O-methyloxime was isolated (0.057 g) as a yellow powder after lyophilisation of the appropriate fractions.

H-RMN (CD$_3$OD): syn isomer: 8.01(s, 1H, CH=N), 7.45(d, 1H, H-8, J=8.7 Hz), 7.04(bt, 1H, H-2pyrrole), 6.93 (d, 1H, H-9), 6.77(m, 1H, H-5pyrrole), 6.52(dd, 1H, H-4pyrrole, J=2.9 and 1.6 Hz), 4.02(bs, 1H, H-4), 3.83(s, 3H, OCH$_3$).

H-RMN (CD$_3$OD): anti isomer: 7.46(d, 1H, H-8, J=8.7 Hz), 7.42(bt, 1H, H-2pyrrole), 7.25(s, 1H, CH=N), 6.94(d, 1H, H-9), 6.76(m, 1H, H-5pyrrole), 6.58(dd, 1H, H-4pyrrole, J=1.6 and 2.9 Hz), 4.02(bd, 1H, H-4, J=1.5 Hz), 3.92(s, 3H, OCH$_3$).

MS (e.s.+): m/z 537.3 (M$^+$+H)

Biological Examples

| MIC (μg/ml) | EXAMPLE 3 | EXAMPLE 4 | EXAMPLE 5 | EXAMPLE 6 |
|---|---|---|---|---|
| S. aureus ATCC 29213 | 0.015 | 0.12 | 0.015 | 0.12 |
| S. aureus GFX01596 Tet R | 0.25 | 0.5 | 0.5 | 0.5 |
| S. pneumoniae 157 | 0.015 | 0.03 | 0.015 | 0.06 |
| S. pneumoniae GFX01778 Tet R | 2 | 2 | 2 | 4 |
| H. influenzae ATCC 49247 | 1 | 2 | 0.5 | 2 |
| M. catarrhalis ATCC 23246 | 0.008 | 0.03 | 0.001 | 0.004 |
| E. coli ML 308-225 | 0.5 | 1 | 0.5 | 2 |

Growth-inhibitory activity was determined on liquid medium by the antibiotic dilution technique using 96-well microtiter system plates containing two-fold dilutions of antibiotic-agent in 0.2 ml. of Mueller-Hinton broth. Plates were inoculated with each test organism to yield a final inoculum of 5×10$^5$ CFU/ml and were incubated aerobically at 37° C. for 18 h. The MIC was defined as the lowest concentration of antibacterial agent that inhibited development of visible growth in the microdilution wells.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A compound of formula (I):

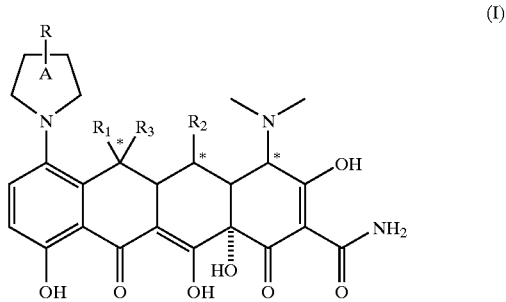

wherein:

A represents an aromatic, 5-membered heterocycle optionally substituted by one or more groups "R" selected from halogen,
—NRaRb,
$C_{1-6}$alkyl,
$C_{2-6}$alkenyl,
$C_{3-6}$alkynyl,
aryl,
heteroaryl,
hydroxy,
—$OC_{1-6}$alkyl,
formyl,
cyano,
trifluoromethyl,
—CHNOR,
—$CO_2$Ra,
—CONRaRb,
—NRaC(O)Ra,
—NRaC(O)ORa,
—OC(O)NRaRb,
—OC(O)Ra,
—OC(O)ORa, or a $C_{1-6}$alkyl group substituted by one or more groups selected from hydroxy,
—NRaRb,
—$OC_{1-6}$alkyl,
—SRa,
—CHNOR,
—$CO_2$Ra,
—CONRaRb,
—NRaC(O)Ra,
—NRaC(O)ORa,
—OC(O)NRaRb,
—OC(O)Ra,
—OC(O)ORa Ra and Rb independently represent hydrogen or $C_{1-6}$alkyl;

$R^1$ represents hydrogen, $C_{1-6}$alkyl or together $R^1$ and $R^3$ represent a $CH_2$ moiety;

$R^2$ represents hydrogen, —$OC_{1-6}$alkyl, —$O(O)C_{1-6}$alkyl or hydroxy;

$R^3$ represents hydrogen, hydroxy or together $R^3$ and $R^1$ represent a $CH_2$ moiety, or a pharmaceutically acceptable salt or solvate thereof.

2. A pharmaceutical formulation comprising a compound of claim 1 and one or more pharmaceutically acceptable carriers.

3. A compound of claim 1, wherein the compound is:

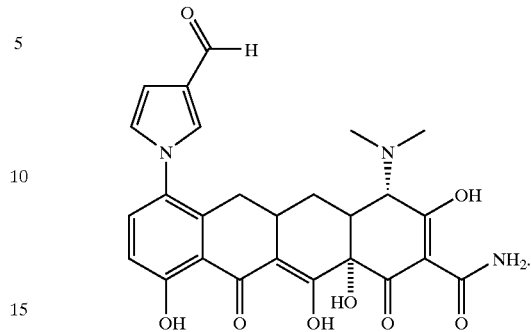

4. The compound of claim 1, wherein A is tetrazole.
5. The compound of claim 4, wherein R is hydrogen.
6. The compound of claim 1, wherein A is triazole.
7. The compound of claim 6, wherein said triazole is 1, 2, 3-triazole.
8. The compound of claim 7, wherein R is CORa.
9. The compound of claim 8, wherein Ra is $C_{1-6}$alkyl.
10. The compound of claim 1, wherein A is pyrrolyl.
11. The compound of claim 10, wherein R is formyl.
12. The compound of claim 10, wherein R is cyano.
13. The compound of claim 10, wherein R is CHNORa.
14. The compound of claim 13, wherein Ra is hydrogen.
15. The compound of claim 13, wherein Ra is methyl.
16. The compound of claim 1, wherein $R_1$, $R_2$, and $R_3$ are each hydrogen.
17. A compound selected from the group consisting of:
[4(R,S)-(4aα,5aα, 12aα)]-4-(Dimethylamino)-7-(1H-Tetrazol-1-yl)-1,4,4a,5,5a,6, 11,12a-octahydro-3,10,12,12a-tetrahydroxy-1,11-dioxo-2-naphthacenecarboxamide;

[4-S-(4aα,5aα, 12aα)]-4-(Dimethylamino)-7-[(4-ethoxycarbonyl)-1H-triazol-1-yl]-1,4,4a,5,5a,6,11,12a-octahydro-3,10,12,12a-tetrahydroxy-1,11-dioxo-2-naphthacenecarboxamide;

[4-S-(4aα,5aα, 12aα)]-4-(Dimethylamino)-7-[(5-ethoxycarbonyl)-1H-triazol-1-yl 1,4,4a,5,5a,6,11,12a-octahydro-3, 10,12,12a-tetrahydroxy-1,11-dioxo-2-naphthacenecarboxamide;

[4S-(4aα,5aα, 12aα)]-4-(Dimethylamino)-7-(1H-pyrrol-1-yl-3-carboxaldehyde)-1,4,4a,5,5a,6,11,12a-octahydro-3, 10,12,12a-tetrahydroxy-1,11-dioxo-2-naphthacenecarboxamide;

[4S-(4aα,5aαα, 12aα)]-4-(Dimethylamino)-7-(3-((hydroxymino)-methyl)-1H-pyrrol-1-yl)-1,4,4a,5,5a,6,11,12a-octahydro-3, 10,12,12a-tetrahydroxy-1,11-dioxo-2-naphthacenecarboxamide;

[4S-(4aα,5aαα, 12aα)]-7-(3-Cyanopyrrol-1-yl)-4-(dimethylamino)-1,4,4a,5,5a,6,11,12a-octahydro-3, 10,12,12a-tetrahydroxy-1,11-dioxo-2-naphthacenecarboxamide; and

[4S-(4aα,5aα, 12aα)]-4-(Dimethylamino)-7-(3-((methyloxymino)methyl)-1H-pyrrol-1-yl)-1,4,4a,5,5a,6,11, 12a-octahydro-3,10,12,12a-tetrahydroxy-1,11-dioxo-2-naphthacenecarboxamide.

* * * * *